United States Patent [19]

Igarashi et al.

[11] Patent Number: 5,179,105

[45] Date of Patent: Jan. 12, 1993

[54] PHENOXYACETIC ACID COMPOUNDS, METHOD FOR PRODUCTION THEREOF, AND PHARMACEUTICAL PREPARATIONS CONTAINING SAME

[75] Inventors: Azuma Igarashi; Sachiko Maeda; Yasuhiro Hirakawa; Katsuyoshi Sugisaki; Shinji Ozawa, all of Ashigarakami, Japan

[73] Assignee: Terumo Kabushiki Kaisha, Tokyo, Japan

[21] Appl. No.: 775,571

[22] Filed: Oct. 15, 1991

[30] Foreign Application Priority Data

Oct. 16, 1990 [JP] Japan .................. 2-278727
Oct. 16, 1990 [JP] Japan .................. 2-278728

[51] Int. Cl.$^5$ .................. A61K 31/47; C07C 303/00; C07C 315/00; C07D 215/38
[52] U.S. Cl. .................. 514/311; 560/12; 560/9; 562/430; 562/426; 514/535; 514/562; 514/522; 546/175; 558/413; 558/415
[58] Field of Search .................. 560/12, 9; 562/430, 562/426; 514/535, 562, 311, 522; 546/175; 558/413, 415

[56] References Cited

U.S. PATENT DOCUMENTS 4,344,883  8/1982  Fahmy et al. .................. 558/413
4,866,196  9/1989  Iwakuma et al. .................. 560/12

*Primary Examiner*—Mary C. Lee
*Assistant Examiner*—Robert C. Whittenbaugh
*Attorney, Agent, or Firm*—Burns, Doane, Swecker & Mathis

[57] ABSTRACT

A phenoxyacetic acid compound represented by the general formula I: t,0010 wherein X is one member selected from the class consisting of hydrogen atom, halogen atoms, lower alkyl groups, trifluoromethyl group, alkoxy groups, hydroxy group, and cyano group, $R^1$ is one member selected from the class consisting of hydrogen atom, methyl group, and ethyl group, n is an integer in the range of from 0 to 2, and Y is

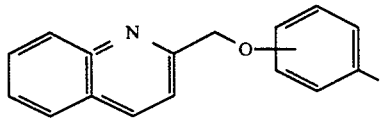

or

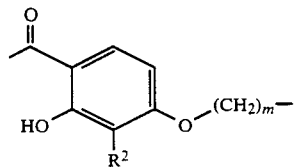

wherein $R^2$ is hydrogen atom or n-propyl group and m is an integer in the range of from 1 to 5, or a pharmaceutically acceptable salt thereof.

16 Claims, No Drawings

PHENOXYACETIC ACID COMPOUNDS, METHOD FOR PRODUCTION THEREOF, AND PHARMACEUTICAL PREPARATIONS CONTAINING SAME

BACKGROUND OF THE INVENTION

1. Field of the Invention

This invention relates to novel phenoxyacetic acid compounds, a method for the production thereof, and pharmaceutical preparations containing these compounds.

2. Description of the Prior Art

Thromboxane $A_2$ and leukotrienes suggest their intimate association with serious ischemic diseases such as cerebral infarot and myocardial infarct and allergic inflammations such as bronchial asthma. Numerous thromboxane $A_2$ antagonists, leukotriene antagonists, and synthetic enzyme inhibitors have been developed in rapid succession to date. Participation of a plurality of chemical mediators in the actual morbidity of these diseases has been demonstrated. The simple use of the existing enzyme inhibitors and receptor antagonists, therefore, cannot be expected to produce a fully satisfactory therapeutic effect. In the circumstances, we have investigated the feasibility of developing a medicine which combines a thromboxane $A_2$ antagonism with a leukotriene antagonism. None of the known compounds constitutes itself a receptor for both thromboxane $A_2$ and leukotrienes and, at the same time, antagonizes them simultaneously. A compound which combines these antagonisms, therefore, can constitute itself a novel type of pharmaceuticals.

A certain kind of phenoxyacetic acid compounds which are useful for prophylaxis and treatment of thrombosis (U.S. Pat. No. 4,866,196).

We synthesized various phenoxyacetic acid compounds and conducted a diligent study on their physiological actions. As a result, we have found that phenoxyacetic acid compounds conforming to this invention possess both the thromboxane $A_2$ antagonism and the leukotriene antagonism. From this knowledge, they have drawn an inference that these compounds can solve the problem encountered by the simple use of synthetic enzyme inhibitors and receptor antagonists as described above.

An object of this invention, therefore, is to provide novel phenoxyacetic acid compounds and a method for the production thereof.

Another object of this invention is to provide pharmaceutical preparations containing phenoxyacetic acid compounds which antagonize both thromboxane $A_2$ and leukotrienes.

SUMMARY OF THE INVENTION

The objects described above are accomplished by phenoxyacetic acid compounds represented by the general formula I:

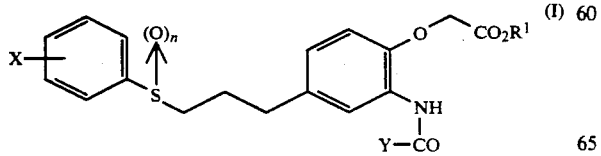

wherein X is one member selected from the class consisting of hydrogen atom, halogen atoms, lower alkyl groups, trifluoromethyl group, alkoxy groups, hydroxyl group, and cyano group, $R^1$ is one member selected from the class consisting of hydrogen atom, methyl group, and ethyl group, n is an integer in the range of from 0 to 2, Y is

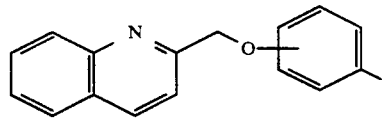

or

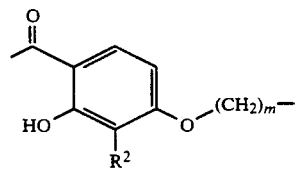

wherein $R^2$ is hydrogen atom or n-propyl group and m is an integer in the range of from 1 to 5, or pharmaceutically acceptable salts thereof.

These objects are accomplished by a method for producing a phenoxyacetic acid compound represented by the general formula I:

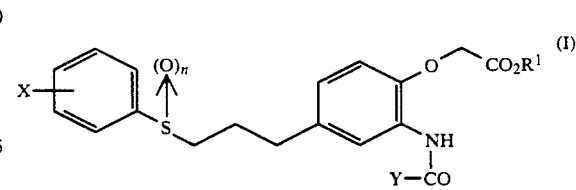

wherein X, n, $R^1$, and Y have the same meanings as defined above, by causing a sulfone compound represented by the general formula II:

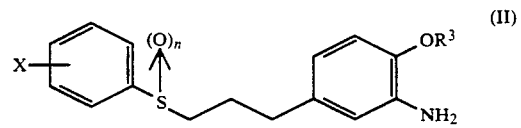

wherein X and n have the same meanings as defined above, $R^3$ is a protective group capable of liberating under a dissociation state, to react with an acid halide represented by the general formula III:

Y—COZ  (III)

wherein Y has the same meanings as defined above and Z is a halogen atom, in the presence of a base, treating the resultant amide compound with a strong acid, causing the produced phenal compound to react with a halogenated alkyl acetate in the presence of a base, and subjecting the ester moiety of the resultant reaction product, when necessary, to alkali hydrolysis.

The objects are accomplished by a pharmaceutical composition which comprises a phenoxyacetic acid compound represented by the general formula I or a physiologically acceptable salt thereof and a physiologically acceptable carrier.

This invention provides novel phenoxyacetic acid compounds and pharmaceutical containing these compounds.

Since the compounds of the present invention are thromboxane $A_2$ antagonists and are leukotriene antagonists as well, they can be used as effective preventive medicines for thrombosis and asthma and other allergic reactions which are diseases associated with thromboxane $A_2$ and leukotrienes.

EXPLANATION OF THE PREFERRED EMBODIMENT

The phenoxyacetic acid compounds which accord with the present invention are novel compounds represented by the general formula I and embrace physiologically acceptable salts of such novel compounds.

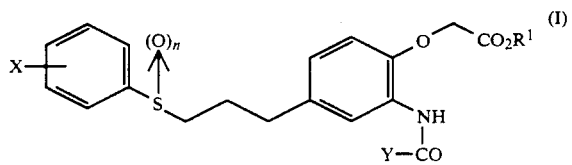

In this formula, X is one member selected from the class consisting of hydrogen atom, halogen atoms, preferably chlorine atom, bromine atom and fluorine atom, lower alkyl groups, preferably alkyl groups of 1 to 4 carbon atoms, more preferably methyl group, trifluoromethyl group, alkoxy groups, preferably alkoxy groups of 1 to 4 carbon atoms, more preferably methoxy group, hydroxyl group, and cyano groups, $R^1$ is one member selected from the class consisting of hydrogen atom, methyl group, and ethyl group, n is an integer in the range of from 0 to 2, preferably 2, and Y is

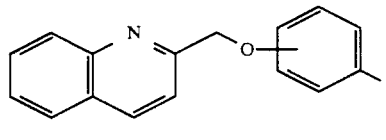

or

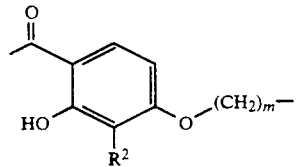

wherein $R^2$ is hydrogen atom or n-propyl group, preferably n-propyl group and m is an integer in the range of from 1 to 5, preferably 3).

As the pharmaceutically acceptable salt within the present invention, there are hydrochloride and salts with inorganic or organic bases, e.g., alkali metal salts such as sodium salts and potassium salts, alkaline earth metal salts such as calcium salts and magnesium salts, heavy metal salts such as zinc salts, ammonium salts, and organic amines such as tromethamine salts triethylamine salts, pyridine salts, ethanolamin salts, and basic amino acid salts.

The phenoxyacetic acid compounds which answer this description include 4-[3-(4-chlorobenzenesulfonyl)-propyl]-2-[4-(2-quinoline methoxy)benzoylamino] ethyl phenoxyacetate, 4-[3-(4-chlorobenzenesulfonyl)-propyl]-2-[4-(2-quinoline methoxy)benzoylamino] phenoxyacetic acid, 4-[3-(4-chlorobenzenesulfonyl)propyl]-2-[3-(2-quinoline methoxy)benzoylamino] ethyl phenoxyacetate, 4-[3-(4-chlorobenzenesulfonyl)propyl]-2-[3-(2-quinoline methoxy)benzoylamino] phenoxyacetic acid, 4-[3-(4-bromobenzenesulfonyl)propyl]-2-[4-(2-quinoline methoxy)benzoylamino] ethyl phenoxyacetate, 4-[3-(4-bromobenzenesulfonyl)propyl]-2-[4-(2-quinoline methoxy)benzoylamino] phenoxyacetic acid, 4-[3-(4-bromobenzenesulfonyl)propyl]-2-[3-(2-quinoline methoxy)benzoylamino] ethyl phenoxyacetate, 4-[3-(4-bromobenzenesulfonyl)propyl]-2-[3-(2-quinoline methoxy)benzoylamino] phenoxyacetic acid, 4-[3-(4-chlorobenzenesulfonyl)propyl]-2-[(4-acetyl-3-hydroxy-2-propyl)phenoxyacetylamino] ethyl phenoxyacetate, 4-[3-(4-chlorobenzenesulfonyl)propyl]-2-[(4-acetyl-3-hydroxy-2-propyl)phenoxyacetylamino] phenoxyacetic acid, 4-[3-(4-chlorobenzenesulfonyl)propyl]-2-[(4-acetyl-3-hydroxy-2-propyl)phenoxy-4-butamide] ethyl phenoxyacetate, 4-[3-(4-chlorobenzenesulfonyl)propyl]-2-[(4-acetyl-3-hydroxy-2-propyl)phenoxy-4-butamide] phenoxyacetic acid, 4-[3-(4-bromobenzenesulfonyl)propyl]-2-[(4-acetyl-3-hydroxy-2-propyl)phenoxyacetylamino] ethyl phenoxyacetate, 4-[3-(4-bromobenzenesulfonylpropyl]-2-[(4-acetyl-3-hydroxy-2-propyl)phenoxyacetylamino] phenoxyacetic acid, 4-[3-(4-bromobenzenesulfonyl)propyl]-2-[(4-acetyl-3-hydroxy-2-propyl)phenoxy-4-butamide] ethyl phenoxyacetate, 4-[3-(4-bromobenzenesulfonyl)propyl]-2-[(4-acetyl-3-hydroxy-2-propyl)phenoxy-4-butamide] phenoxyacetic acid, 4-[3-(4-chlorobenzenesulfonyl)propyl]-2-[(4-acetyl-3-hydroxy)phenoxyacetylamino] ethyl phenoxyacetate, 4-[3-(4-chlorobenzenesulfonyl)propyl]-2-[(4-acetyl-3-hydroxy)phenoxyacetylamino] phenoxyacetic acid, 4-[3-(4-bromobenzenesulfonyl)propyl]-2-[(4-acetyl-3-hydroxy)phenoxyacetylamino] ethyl phenoxyacetate, 4-[3-(4-bromobenzenesulfonyl)propyl]-2-[(4-acetyl-3-hydroxy)phenoxyacetylamino] phenoxyacetic acid, 4-[3-(4-chlorobenzenesulfonyl)propyl]-2-[(4-acetyl-3-hydroxy)phenoxy4-butamide] ethyl phenoxyacetate, 4-[3-(4-chlorobenzenesulfonyl)propyl]-2-[(4-acetyl-3-hydroxy)phenoxy4-butamide] phenoxyacetic acid, 4-[3-(4-bromobenzenesulfonyl)propyl]-2-[(4-acetyl-3-hydroxy)phenoxy4-butamide] ethyl phenoxyacetate, and 4-[3-(4-bromobenzenesulfonyl)propyl]-2-[(4-acetyl-3-hydroxy)phenoxy4-butamide] phenoxyacetic acid, 4-[3-(4-methoxybenzenesulfonyl)propyl]-2-[4-(2-quinoline methoxy)benzoylamino] ethyl phenoxyacetate, 4-[3-(4-methoxybenzenesulfonyl)propyl]-2-[4-(2-quinoline methoxy)benzoylamino] phenoxyacetic acid, 4-[3-(4-methoxybenzenesulfonyl)propyl]-2-[3-(2-quinoline methoxy)benzoylamino] ethyl phenoxyacetate, 4-[3-(4-methoxy benzenesulfonyl)propyl]-2-[3-(2-quinoline methoxy)benzoylamino] phenoxyacetic acid, 4-[3-(4-methoxybenzenesulfonyl)propyl]-2-[4-(2-quinoline methoxy)benzoylamino] ethyl phenoxyacetate, 4-[3-(4-hydroxybenzenesulfonyl)propyl]-2-[4-(2-quinoline methoxy)benzoylamino] phenoxyacetic acid, 4-[3-(4-hydroxybenzenesulfonyl)propyl]-2-[3-(2-quinoline methoxy)benzoylamino] ethyl phenoxyacetate, 4-[3-(4-hydroxybenzenesulfonyl)propyl]-2-[3-(2-quinoline methoxy)benzoylamino] phenoxyacetic acid, 4-[3-(4-methoxybenzenesulfonyl)propyl]-2-[(4-acetyl-3-hydroxy-2-propyl)phenoxyacetylamino] ethyl phenoxyacetate, 4-[3-(4-methoxybenzenesulfonyl)propyl]-2-[(4-acetyl-3-hydroxy-2-propyl)phenoxyacetylamino] phenoxyacetic acid, 4-[3-(4-methoxybenzenesulfonyl)propyl]-2-[(4-acetyl-3-hydroxy-2-propyl)phenoxy-4- butaminde] ethyl phenoxyacetate, 4-[3-(4-methoxybenzenesulfonyl)propyl]-2-[(4-acetyl-3-hydroxy-2-propyl)phenoxy-4-butamide] phenoxyacetic acid, 4-[3-(4-hydroxybenzenesulfonyl)propyl]-2-[(4-acetyl-3-hydroxy-2-propyl)phenoxyacetylamino] ethyl phenoxyacetate, 4-[3-(4-hydroxybenzenesulfonyl)propyl]-2-[(4-acetyl-3-hydroxy-2-propyl)phenoxyacetylamino] phenoxyacetic acid, 4-[3-(4-hydroxybenzenesulfonyl)propyl]-2-[(4-acetyl-3-hydroxy-2-propyl)phenoxy-4-butamide] ethyl phenoxyacetate, 4-[3-(4-hydroxybenzenesulfonyl)propyl]-2-[(4-acetyl-3-hydroxy-2-propyl)phenoxy-4-butamide] phenoxyacetic acid, 4-[3-(4-ethylbenzenesulfonyl)propyl]-2-[(4-acetyl-3-hydroxy)phenoxyacetylamino] ethyl phenoxyacetate, 4-[3-(4-ethylbenzenesulfonyl)propyl]-2-[(4-acetyl-3-hydroxy)phenoxyacetylamino] phenoxyacetic acid, 4-[3-(4-ethylbenzenesulfonyl)propyl]-2-[(4-acetyl-3-hydroxy-2-propyl)phenoxyacetylamino] ethyl phenoxyacetate, 4-[3-(4-ethylbenzenesulfonyl)propyl]-2-[(4-acetyl-3-hydroxy-2-propyl)phenoxyacetylamino] phenoxyacetic acid, 4-[3-(4-fluorobenzenesulfonyl)propyl]-2-[(4-acetyl-3-hydroxy)phenoxy-4-butamide] ethyl phenoxyacetate, 4-[3-(4-fluorobenzenesulfonyl)propyl]-2-[(4-acetyl-3-hydroxy)phenoxy-4-butamide] phenoxyacetic acid, for example.

Such a phenoxyacetic acid compound represented by the general formula I as described above is obtained by causing a sulfone compound represented by the general formula II:

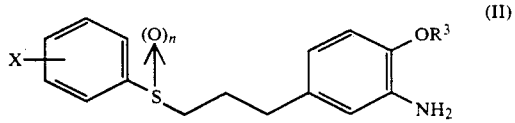

wherein X and n have the same meanings as defined above, $R^3$ is a protective group capable of liberating under a dissociation state, preferably methoxymethyl, 2-methoxyethoxymethyl, or tetrahydropyranyl, to react with an acid halide represented by the general formula III:

wherein Y has the same meaning as defined above and Z is halogen atom, preferably chlorine atom, or bromine atom, and most preferably chlorine atom) in the presence of a base, treating the resultant amide compound with a strong acid, causing a phenol compound to react with a halogenated alkyl acetate in the presence of a base, and subjecting the ester moiety of the resultant reaction product, when necessary, to alkali hydrolysis.

The reaction of the sulfone compound represented by the general formula II with the acid halide represented by the general formula III is carried out by using the acid halide in a proportion in the range of from 1 to 3 mols, preferably from 1 to 1.1 mol, per mol of the sulfone compound and a reaction temperature in the range of from 0° C. to a reflux temperature, preferably from 0° to 25° C. In this reaction, the base is used in a proportion in the range of from 1 to 5 mol, preferably from 2 to 3 mol, per mol of the phenoxyacetic compound. The bases which are effectively usable in this reaction include sodium hydride, potassium carbonate, triethyl amine, for example.

The treatment of the amide compound with a strong acid is carried out at a temperature in the range of from 0° C. to a reflux temperature, preferably from 25° (room temperature) to 50° C. The strong acids which are effectively usable for this treatment include hydrochloric acid, acetic acid-sulfuric acid, born trifluoride, titanium tetrachloride etc. for example. The amount of the strong acid to be used in the treatment is in the range of from 0.1 to 5 mols, preferably from 1 to 2 mols, per mol of the amide compound. The reaction with the halogenated alkyl acetate is carried out by using this alkyl acetate in a proportion in the range of from 1 to 5 mols, preferably from 1.5 to 2 mols, per mol of the phenol compound and a temperature in the range of from 0° to are flux temperature, preferably from 15° to 30° C. The halogenated alkyl acetates which are effectively usable herein include methyl bromoacetate, ethyl bromoacetate, t-butyl bromoacetate, and methyl chloroacetate, for example. The bases which are effectively usable herein are the same as cited above. The amount of the base to be used is in the range of from 1 to 3 mols, preferably from 1 to 1.2 mol, per mol of the phenol compound. Of the reaction product consequently obtained, the ester moiety may be subjected, when necessary, to alkali hydrolysis. The alkalis which are usable effectively for this hydrolysis include sodium hydroxide, potassium hydroxide, and lithium hydroxide, for example. The amount of the alkali to be used for the hydrolysis is in the range of from 1 to 3 mols, preferably from 1 to 1.5 mol, per mol of the phenoxyacetate. The reaction temperature of the alkali hydrolysis is in the range of from 0° C. to a reflux temperature, preferably from 0° to 25° C.

The aforementioned sulfone compounds represented by the general formula II are obtained by subjecting 4-methoxymethoxy-3-nitrobenzaldehyde and trimethyl phosphonoacetate to the Wittig-Horner reaction, reducing the produced methyl 4-methoxymethoxy-3-nitro cinnamate with diisobutyl aluminum hydride, then chlorinating the product of reduction, converting the product of chlorination through condensation with varying thiophenols into 5-[(3-phenylthio)-1-propenyl]-2-methoxymethoxy nitrobenzene derivatives, optionally oxidizing the derivatives by the use of m-chloroperbenzoic acid, and subsequently subjecting the resultant oxidized derivatives to catalytic reduction.

Of the aforementioned acid halides represented by the general formula III, quinoline compounds represented by the general formula IV:

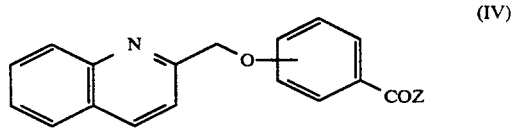

are obtained by causing 2-chloromethyl quinoline to react with varying isomeric hydroxybenzoic esters in the presence of a suitable base, subsequently hydrolyzing the reaction products, and chlorinating carboxylic acids consequently produced by the hydrolysis. These reactions are preferable to be carried out by using such solvents as methylene chloride, tetrahydrofuran, N,N-dimethyl formamide, acetone, and diethyl ether and such reaction temperatures as ranging from 0° C. to relevant refluxing temperatures.

Further, of the aforementioned acid halides represented by the general formula III, pheonol compounds represented by the general formula V:

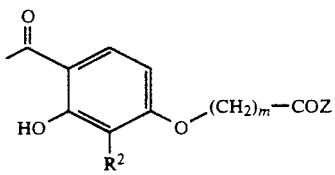 (V)

are obtained by causing 4-acetyl-3-hydroxy-2-propylphenol to react with varying halogenated alkanoic esters such as ethyl bromoacetate in the presence of a suitable base, subsequently subjecting the products of reaction to hydrolysis, and chlorinating the resultant carboxylic acids. These reactions are preferably to be carried out by using such solvents as methylene chloride, tetrahydrofuran, N,N-dimethyl formamide, and acetone and reaction temperatures ranging from 0° C. to relevant refluxing temperatures.

The phenoxyacetic acid compounds of this invention are used as thromboxane $A_2$ antagonists and leukotriene antagonists. Though their dosages are variable with the morbidity of a disease under treatment, they are generally in the range of from 10 to 2,000 mg, preferably 20 to 600 mg, per adult per day. They are preferable to be administered one to three times daily, depending on the seriousness of disease. They can be administered in any desired manner to suit occasion. The oral administration is particularly desirable and the intravenous injection is permissible.

The compound of this invention, as an effective component or as one of the effective components, is used independently or in combination with a pharmaceutically acceptable carrier or excipient as conventionally practiced and is used in various forms such as tablets, sugar-coated tablets, powder, capsules, granules, suspension, emulsion, and injection, for example. The carriers or excipients which are effectively usable for the formulation include calcium carbonate, calcium phosphate, starch, grape sugar, milk sugar, dextrin, alginic acid, mannitol, talc, and magnesium stearate, for example.

Acute toxicity

The compounds of the present invention were tested for acute toxicity by oral administration thereof to ICR type male mice (5 weeks old). Their $LD_{50}$ values were found to be not less than 300 mg/kg. These lethal dosages, compared with their efficacious dosages, indicate high safety of their use for medicines.

Now, this invention will be described more specifically hereinbelow with reference to working examples and test examples. It should be noted, however, that this invention is not limited in any sense to these examples.

EXAMPLE 1

(1) Under a current of argon, a solution of 5.0 g of 4-hydroxy-3-nitrobenzaladehyde in 60 ml of methylene chloride and 6.8 ml of N,N-diisopropyl ethylamine added thereto as kept cooled with ice were stirred for 10 minutes. The produced mixture and 15.6 ml of chloromethylmethyl ether added thereto were stirred at normal room temperature for 10 hours. The resultant reaction mixture was combined with water and extracted from methylene chloride. The consequently separated organic layer was washed sequentially with dilute hydrochloric acid, saturated saline solution, a saturated aqueous sodium hydrogen carbonate solution, and saturated saline solution in the order mentioned and then dried with anhydrous magnesium sulfate. The residue from drying was concentrated under a vacuum and the resultant concentrate was recrystallized from chloroform, to obtain 1.64 g of 4-methoxymethoxyl-3-nitrobenzaldehyde in the form of yellow crystals. The yield was 83%.

(2) Under a current of argon, a solution having 832 mg of sodium hydride suspended in 60 ml and a solution of 4.17 g of trimethyl phosphonoacetate in 15 ml of tetrahydrofuran added thereto as kept cooled with ice were stirred for 30 minutes and the resultant mixture and a solution of 4.39 g of 4-methoxymethoxy-3-nitrobenzaldehyde in 15 ml of tetrahydrofuran added thereto were stirred for eight hours with the temperature raised to room temperature in the meantime. The produced reaction mixture was combined with water and extracted from ethyl acetate. The consequently separated organic layer was washed with saturated saline solution and dried with anhydrous sodium sulfate. The residue from drying was concentrated under a vacuum. The resultant concentrate was subjected to silica gel column chromatography. From the hexane-ethyl acetate (3:1 V/V) eluate, 4.52 g of methyl 4-methoxymethoxy-3-nitrocinnamate was obtained in the form of yellow crystals. The yield was 81%.

(3) Under a current of argon, a solution of 710 mg of methyl 4-methoxymethoxy-3-nitrocinnamate in 6 ml of toluene and 4.4 ml of diisobutyl aluminum hydride (1.5M toluene solution) added thereto at −78° C. were stirred for 30 minutes. The produced reaction solution was combined with methanol at −78° C. to effect decomposition of excess diisobutyl aluminum hydride and then the resultant mixture and water added thereto at 0° C. were stirred for a while. Subsequently, the mixture was filtered with sellaite and wased with ethyl acetate and the filtrate was extracted from ethyl acetate. The consequently separated organic layer was washed with saturated saline solution and then with anhydrous sodium sulfate and concentrated under a vacuum. The resultant concentrate was subjected to silica gel column chromatography. From the hexane-ethyl acetate (1:1 V/V) eluate, 560 mg of 4-methoxymethoxy-3-nitrocinnamyl alcohol was obtained in the form of a yellow oily substance. The yield was 88%.

(4) Under a current of argon, a solution of 1.50 g of 4-methoxymethoxy-3-nitrocinnamyl alcohol in 15 ml of dimethyl formamide and 292 mg of anhydrous lithium chloride and 0.9 ml of 2,4,6-collidine added thereto as kept cooled with ice were stirred for 10 minutes and the produced mixture and 0.5 ml of methanesulfonyl chloride added as kept cooled with ice were stirred for four hours. The resultant reaction mixture was combined with water and extracted from ethyl acetate. The consequently separated organic layer was washed with saturated saline solution and dried with anhydrous sodium sulfate. By concentrating the residue from drying under a vacuum, 1.62 g of 4-methoxymethoxy-3-nitrocinnamyl chloride was obtained in the form of a colorless oily substance. This product was put to use in its unpurified form in the following reaction.

(5) Under a current of argon, a solution having 251 mg of sodium hydride suspended in 10 ml of tetrahydrofuran and 906 mg of p-chlorothiophenol added thereto as kept cooled with ice were stirred for 30 minutes and the produced mixture and a solution of 1.62 g of 4-methoxymethoxy-3-nitrocinnamyl chloride in 5 ml tetrahydrofuran added thereto were stirred at normal room temperature for 14 hours. The resultant reaction mixture was combined with water and extracted from ethyl acetate. The consequently separated organic layer was washed with saturated saline solution and dried with anhydrous sodium sulfate. The residue from drying was concentrated under a vacuum. The concentrate was subjected to silica gel column chromatography. From the hexane-ethyl acetate (5:1 V/V) eluate, 1.77 g of 5-[3-(4-chlorophenylthio)-1-propenyl]-2-methoxymethoxy nitrobenzene was obtained in the form of a colorless oily substance. The yield was 77%.

(6) Under a current of argon, a solution of 300 mg of 5-[3-(4-chlorophenylthio)-1-propenyl]-2-methoxymethoxy nitrobenzene in 6 ml of methylene chloride and 283 mg of m-chloroperbenzoic acid added thereto as kept cooled with ice were stirred for eight hours. The reaction mixture was combined with water and extracted from ethyl acetate. The consequently separated organic layer was washed sequentially with a saturated aqueous sodium hydrogen carbonate solution and saturated saline solution in the order mentioned and then dried with anhydrous sodium sulfate. The residue from drying was concentrated under a vacuum and the concentrate was subjected to silica gel column chromatography. From the hexane-ethyl acetate (2:1 V/V) eluate, 240 mg of 5-[3-(4-chlorophenylsulfonyl)-1-propenyl]-2-methoxymethoxy nitrobenzene was obtained in the form of yellow crystals. The yield was 74%.

(7) Under a current of argon, a solution of 2.0 g of 4-acetyl-3-hydroxy-2-propylphenol in 15 ml of acetone and 1.44 g of potassium carbonate added thereto at 0° C. were stirred for 10 minutes and then the produced mixture and a solution of 1.91 g of ethyl bromoacetate in 5 ml of acetone added thereto were stirred at normal room temperature for 15 hours. The reaction mixture was combined with water and extracted from ethyl acetate. The consequently separated organic layer was washed with saturated saline solution and then dried with anhydrous sodium sulfate. The residue from drying was concentrated under a vacuum. The concentrate was subjected to silica gel column chromatography. From the hexane-ethyl acetate (4:1 V/V) eluate, 2.73 g of 4-acetyl-3-hydroxy-2-propylethyl phenoxyacetate was obtained in the form of white crystals. The yield was 94%.

(8) Under a current of argon, a solution of 2.73 g of 4-acetyl-3-hydroxy-3-propylethyl phenoxyacetate in 8 ml of ethanol and 4 ml of tetrahydrofuran and 8 ml of an aqueous 2N sodium hydroxide solution added thereto as kept cooled with ice were stirred for 10 hours. The resultant reaction mixture was concentrated under a vacuum and the produced concentrate was acidified by addition of 2N hydrochloric acid. By separating the precipitated crystals by filtration and drying the crystals, 2.19 g of 4-acetyl-3-hydroxy-2-propyl phenoxyacetic acid was obtained in the form of reddish brown crystals. The yield was 89%.

(9) Under one atmosphere, a solution of 300 mg of 5-[3-(4-chlorophenylsulfonyl)-1-propenyl]-2-methoxymethoxy nitrobenzene in 8 ml of ethyl acetate and 500 mg of 10% palladium carbon added thereto were stirred in the presence of hydrogen gas. The resultant reaction mixture was filtered and then concentrated under a vacuum, to produce 220 mg of 5-[3-(4-chlorobenzenesulfonyl)propyl]-2-methoxymethoxy aniline in the form of a colorless oily substance. The yield was 73%. This product was put to use in its unpurified form in the following reaction.

(10) Under a current of argon, a solution of 151 mg of 4-acetyl-3-hydroxy-2-propyl phenoxyacetic acid in 3 ml of methylene chloride and 127 mg of 1-ethylene-3-(3-dimethylaminopropyl) carbodiimide hydrochloride added thereto as kept cooled with ice were stirred for 10 minutes and the produced mixture and a solution of 220 mg of 5-[3-(4-chlorobenzenesulfonyl)propyl]-2-methoxymethoxy aniline in 3 ml of methylene chloride added thereto were stirred for 12 hours. The reaction mixture was combined with water and extracted from methylene chloride. The consequently separated organic layer was washed with saturated saline solution and dried with anhydrous magnesium sulfate. The residue from drying was concentrated under a vacuum and the resultant concentrate was subjected to silica gel column chromatography. From the hexane-ethyl acetate (2:1 V/V) eluate, 120 mg of 5-[3-(4-chlorobenzenesulfonyl)propyl]-2-methoxymethoxy-N-[(4-acetyl-3-hydroxy-2-propyl)phenoxyacetyl] aminobenzene was obtained in the form of white crystals. The yield was 33%.

(11) Under a current of argon, a solution of 120 mg of 5-[3-(4-chlorobenzenesulfonyl)propyl]-2-methoxymethoxy-N-[(4-acetyl-3-hydroxy-2-propylphenoxyacetyl] aminobenzene in 3 ml of methanol and 4 ml of tetrahydrofuran and 1 ml of 6N hydrochloric acid added thereto were stirred at 50° C. for one hour. The reaction mixture was combined with water and extracted from ethyl acetate. The consequently separated organic layer was washed with saturated saline solution and dried with anhydrous sodium sulfate. The residue from drying was concentrated under a vacuum and the resultant concentrate was subjected to silica gel column chromatography. From the hexane-ethyl acetate (1:1 V/V) eluate, 100 mg of 4-[3-(4-chlorobenzenesulfonyl)propyl]-2-(4-acetyl-3-hydroxy-2-propylphenoxyacetylamino) phenol was obtained in the form of white crystals. The yield was 89%.

(12) Under a current of argon, a solution of 100 mg of 4-[3-(4-chlorobenzenesulfonyl)propyl]-2-[(4-acetyl-3-hydroxy-2-propyl)phenoxyacetylamino] phenol in 8 ml of acetone and 25 mg of potassium carbonate added thereto as kept cooled with ice were stirred for five minutes and the produced mixture and a solution of 33 mg of ethyl bromoacetate in 2 ml of acetone added thereto were stirred at normal room temperature for 15 hours. The reaction mixture was combined with water and extracted from ethyl acetate. The consequently separated organic layer was anhydrous sodium sulfate. The residue from drying was concentrated under a vacuum and the resultant concentrate was subjected to silica gel column chromatography. From the hexane-ethyl acetate (2:1 V/V) eluate, 110 mg of 4-[3-(4-chlorobenzenesulfonyl)propyl]-2-[(4-acetyl-3-hydroxy-2-propyl)phenoxyacetylamino] ethyl phenoxyacetate was obtained in the form of white crystals. The yield was 95%. The spectroscopic data obtained of this product suggest the structure of the following formula (VI).

MMR(CDC l$_3$) δ:1.87(3H, t, J=7 HZ), 1.18(3H, t, J=6 HZ), 1.48-2.24(4H, m), 2.39-3.24(6H, m), 2.51(3H, S), 4.15(2H, q,J=6 HZ), 4.60(4H,S), 6.39(1H, d, J=9 HZ), 6.72(2H, brS), 7.33-7.83(5H, m), 8.12(1H, brS), 9.00(1H, brS), 12.83(1H, S)

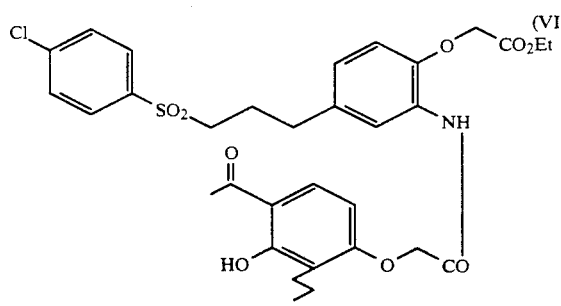

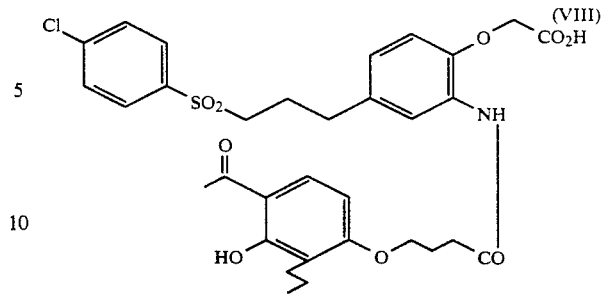

(13) Under a current of argon, a solution of 110 mg of 4-[3-(4-chlorobenzenesulfonyl)propyl]-2-[(4-acetyl-3-hydroxy-2-propyl)phenoxyacetylamino] ethyl phenoxyacetate in 1 ml of tetrahydrofuran and 1 ml of an aqueous 2N sodium hydroxide solution added thereto as kept cooled with ice were stirred for two hours. The reaction mixture was concentrated under a vacuum. The resultant concentrate was acidified by addition of 1N hydrochloric acid and then extracted from ethyl acetate. The consequently separated organic layer was washed with water and dried with anhydrous sodium sulfate. The residue from drying was concentrated under a vacuum. The produced concentrate was subjected to silica gel column chromatography. From the methylene chloride-methanol (10:1 V/V) eluate, 50 mg of 4-[3-(4-chlorobenzenesulfonyl)propyl]-2-[(4-acetyl-3-hydroxy-2-propyl)phenoxyacetylamino] phenoxyacetic acid was obtained in the form of white crystals. The yield was 48%. The spectroscopic data obtained of this product support the structure of the following formula VII.

$IR_{max}^{kBr}$ cm$^{-1}$: 3380(—OH), 1620(—CO$_2$H)

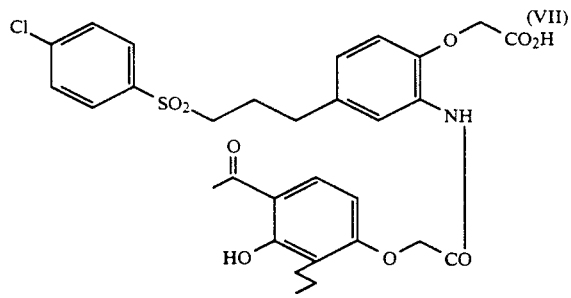

EXAMPLE 2

4-[3-(4-Chlorobenzenesulfonyl)propyl]-2-[(4-acetyl-3-hydroxy-2-propyl)phenoxy-4-butamide] phenoxyacetic acid was obtained by following the procedure of Example 1 using 4-acetyl-3-hydroxy-3-propylphenoxy-1-butyric acid and 5-[3-(4-chlorobenzenesulfonyl)-propyl]-2-methoxymethoxy aniline under a current of argon. The spectroscopic data obtained of this product support the structure of the following formula (VIII).

MMR(CDC l$_3$)δ: 0.90(3H, t, J=7 HZ), 1.57(3H, t, J=7 HZ), 1.42-3.18(14H, m), 2.51(3H,S), 4.15(2H, t, J=7 HZ), 4.51(4H,s), 6.36(1H, d, J=9 HZ), 6.69(2H, S), 7.15-7.81(5H, m), 8.09(1H.brS), 8.45(1H, brS), 12.51(1H, S)

EXAMPLE 3

(1) Under a current of argon, a solution of 3.02 g of ethyl 4-hydroxybenzoate in 80 ml of acetone and 4.22 g of 2-(chloromethyl) quinoline hydrochloride, 12.84 g of cesium carbonate, and 65 mg of potassium iodide added separately thereto were reflexed at 80° C. for 11 hours. The reaction mixture was filtered with sellaite and washed with acetone. The filtrate was concentrated under a vacuum. The residue from the concentration was subjected to silica gel column chromatography. From the hexane-ethyl acetate (4:1 V/V) eluate, 4.64 g of 4-(2-quinoline methoxy) methyl benzoate was obtained in the form of white crystals. The yield was 80%.

(2) Under a current of argon, a solution of 2.32 g of 4-(2-quinoline methoxy) benzoin acid in 12 ml of tetrahydrofuran and an aqueous 1N sodium hydroxide solution added thereto were reflexed at 90° C. for 14 hours. The reaction mixture was concentrated under a vacuum. The residue from the concentration was adjusted by addition of 1N hydrochloric acid to a pH value of about 4. When the crystals consequently precipitated were filtered and the residue of filtration was dried under a vacuum, 1.86 g of 4-(2-quinoline methoxy) benzoin acid was obtained in the form of white crystals. The yield was 78%.

(3) Under a current of argon, 294 mg of 4-(2-quinoline methoxy) benzoin acid kept cooled with ice and 2 ml of thionyl chloride added thereto were stirred for 2.5 hours. 4-(2-Quinoline methoxy) benzoyl chloride obtained in the form of white crystals by concentrating the resultant reaction mixture under a vacuum and drying the concentrated reaction mixture was used in its unpurified form in the following reaction.

Under a current of argon, a solution of the aforementioned 4-(2-quinoline methoxy)benzoyl chloride in 3 ml of chloroform kept cooled with ice and 0.81 ml of triethyl amine added thereto were stirred for 10 minutes and then the resultant mixture and 2 ml of chloroform solution of 360 mg of 5-[3-(4-chlorobenzenesulfonyl)-propyl]-2-methxymethoxy aniline added thereto were stirred at normal room temperature for 16 hours. The resultant reaction mixture was combined with water and extracted from methylene chloride. The organic layer consequently obtained was washed with saturated saline solution and dried with anhydrous magnesium sulfate. The product from the drying was concentrated under a vacuum and the residue of concentration was subjected to silica gel column chromatography. From the hexane-ethyl acetate (1:1 V/V) eluate consequently obtained, 290 mg of 5-[3-(4-chlorobenzenesulfonyl)-propyl]-2-methoxymethoxy-N-[4-(2-quinoline methoxy)benzoyl] aminophenol was separated in the form of white crystals. The yield was 36%.

(4) Under a current of argon, a solution of 290 mg of 5-[3-(4-chlorobenzenesulfonyl)propyl]-2-methoxymethoxy-N-[4-(2-quinoline methoxy)benzoyl] aminophenol in 3 ml of methanol and 5 ml of tetrahydrofuran and 1 ml of 6N hydrochloric acid added thereto were stirred at 50° C. for two hours. By diluting the resultant reaction mixture with ethyl acetate and drying the consequently precipitated crystals under a vacuum, 200 mg of 4-[3-(4-chlorobenzenesulfonyl)-propyl]-2-[4-(2-quinoline methoxy)benzoylamino] phenol was obtained in the form of yellow crystals. The yield was 74%.

(5) Under a current of argon, a solution of 200 mg of 4-[3-(4-chlorobenzenesulfonyl)propyl]-2-[4-(2-quinoline methoxy)benzoylamino] phenol in 15 ml of acetone and 47 mg of potassium carbonate added thereto as kept cooled with ice were stirred for 10 minutes. Then, the resultant mixture and a solution of 62 mg of ethyl bromoacetate in 5 ml of acetone added thereto were stirred at normal room temperature for 12 hours. The produced reaction mixture was combined with water and extracted from ethyl acetate. The organic layer consequently separated was washed with saturated saline solution and dried with anhydrous sodium sulfate. The residue from the drying was concentrated under a vacuum and then the resultant concentrate was subjected to silica gel column chromatography. From the hexane-ethyl acetate (1:1 V/V) eluate, 180 mg of 4-[3-(4-chlorobenzenesulfonyl)propyl]-2-[4-(2-quinoline methoxy)benzoylamino] ethyl phenoxyacetate was obtained in the form of white crystals. The yield was 79%. The spectroscopic data obtained of the product support the structure of the following formula (IX).

MMR(CDC l$_3$)δ: 1.30(3H, t, J=7 HZ), 1.80-2.28(2H, m), 2.67(2H, t, J=6 HZ), 2.94-3.21(2H, m), 4.29(2H, q, J=8 HZ), 4.70(2H, S), 5.48(2H, S), 6.73-8.37(17H, m), 9.10(1H, S)

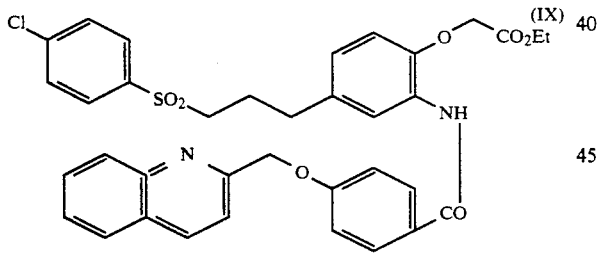

(6) Under a current of argon, a solution of 180 mg of 4-[3-(4-chlorobenzenesulfonyl)propyl]-2-[4-(2-quinoline methoxy)benzoylamino] ethyl phenoxyacetate in 2 ml of tetrahydrofuran and 1 ml of an aqueous 2N sodium hydroxide solution added thereto as kept cooled with ice were stirred for two hours. The produced reaction mixture was concentrated under a vacuum. The resultant concentrate was adjusted by addition of 1N hydrochloric acid to a pH value of about 4. The consequently precipitated crystals were separated by filtration, dried, and then subjected to silica gel column chromatography. From the ethylene chloride-methanol (10:1 V/V) eluate, 130 mg of 4-[3-(4-chlorobenzenesulfonyl)-propyl]-2-[4-(2-quinoline methoxy)benzoylamino] phenoxyacetic acid was obtained in the form of white crystals. The yield was 75%. The spectroscopic data obtained of the product support the structure of the following formula (X).

MMR(CDC l$_3$)δ: 1.47-4.66(8H, m), 5.44(2H, S,), 6.70-8.54(18H, m), 11.95(1H, S)

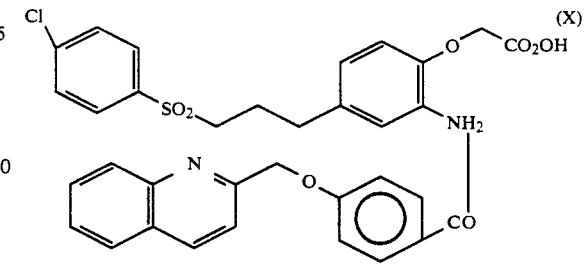

EXAMPLE 4

4-[3-(4-Chlorobenzenesulfonyl)propyl]-2-[3-(2-quinoline methoxy)benzoylamino] phenoxyacetic acid was obtained by following the procedure of Example 1 using 3-(2-quinoline methoxy) benzoin acid and 5-[3-(4-chlorobenzenesulfonyl)proplyl]-2-methoxymethoxy aniline under a current of argon. The spectroscopic data obtained of this product support the structure of the following formula (XI).

MMR(CDC l$_3$)δ: 1.85-2.22(2H, m), 2.60-2.85(2H, m), 4.68(2H, S), 5.50(2H, S), 6.75-8.40(17H, m)

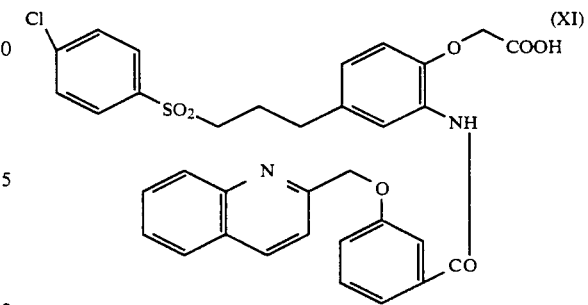

EXAMPLE 5

1.0 g 4-[3-(4-chlorobenzeneaulfonyl) propyl]-2-[3-(2-quinolinemethozy)benzoylamino] phenoxyacetic acid was added to 150 ml of ethanol to obtain a mixture, and 207 mg of tris(hydroxymethyl) aminomethane was added to the mixture under a current of argon at a temperature of 25° C., and them it was heated at a temperature of 100° C. under reflux for 2.5 hours. After distilling off ethanol 1.19 of tromethamine salt of 4-[3-(4-chlorobenzenesulfonyl) propyl]-2-[3-2-quinolinemethoxy)benzoylamino] phenoxyacetic acid was obtained as white crystal.

Text Example

Compounds of the present invention indicated in Table 1 exhibited in vitro antagonistic actions to thromboxane A$_2$ and leukotriene D$_4$ as shown in Table 1.

The IC50 values indicative of the in vitro antagonistic actions of the compounds of this invention to thromboxane A$_2$ and leukotriene D$_4$ were determined by the use of the following test system.

Bronchial segments and ileal segments excised from Hartley type male guinea pigs 350 to 450 g in body weight were suspended under respective loads of 0.3 g and 0.5 g in Magnus baths containing Tyrode solution and kept exposed to passage therethrough of a mixed gas consisting of 95% of oxygen and 5% of carbon dioxide. After the suspended segments were stabilized for about one hour, U-46619 (equivalent to thromboxane $A_2$, produced by Kaiman K. K.) was added in a concentration of $10^{-7}$ to the bath containing the bronchial segments and leukotriene $D_4$ (produced by Wako Pure Chemicals Co., Ltd.) in a concentration of $10^{-8}$M to the bath containing the bronchial segments. In contrast to the amounts of shrinkage produced in the bronchial segments and ileal segments, the amounts of shrinkage produced by U-46619 in the bronchial segments and the amounts of shrinkage produced by leukotriene $D_4$ in the ileal segments both in the presence of the compounds of this invention added in varying concentrations were measured. The $IC_{50}$ values were computed based on the results of the measurement.

TABLE 1

| Compound | antagonistic action to $T_xA_2$ | antagonistic action to $LTD_4$ |
|---|---|---|
| [structure] | $4.5 \times 10^{-9}$ | $3.8 \times 10^{-6}$ (ileal) |
| [structure] | $5.0 \times 10^{-8}$ | $4.3 \times 10^{-7}$ (ileal) $3.7 \times 10^{-7}$ (bronchial) |
| [structure] | $2.6 \times 10^{-8}$ | $3.7 \times 10^{-7}$ (ileal) |
| [structure] | $5.7 \times 10^{-8}$ | $1.3 \times 10^{-9}$ (ileal) $6.4 \times 10^{-8}$ (bronchial) |

TABLE 1-continued

| Compound | antagonistic action to $T_xA_2$ | antagonistic action to $LTD_4$ |
|---|---|---|
| 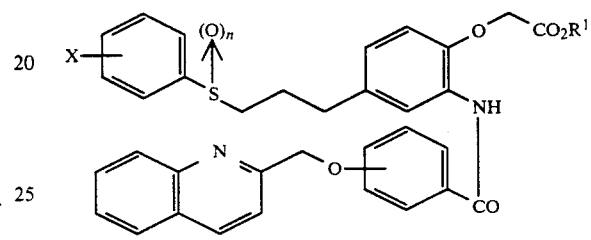 | $3.0 \times 10^{-8}$ | $1.5 \times 10^{-7}$ (bronchial) |

What is claimed is:

1. A phenoxyacetic acid compound represented by the general formula I:

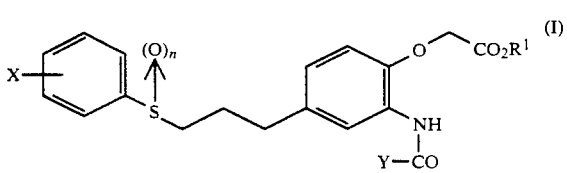
(I)

wherein X is one member selected from the class consisting of hydrogen atom, halogen atoms, lower alkyl groups, trifluoromethyl group, alkoxy groups, hydroxyl group, and cyano group, $R^1$ is one member selected from the class consisting of hydrogen atom, methyl group, and ethyl group, n is an integer in the range of from 0 to 2, and Y is

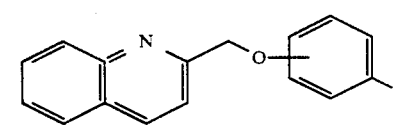

or

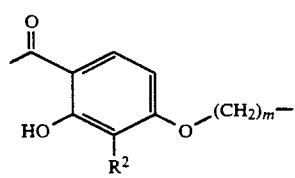

wherein $R^2$ is hydrogen atom or n-propyl group and m is an integer in the range of from 1 to 5, or a pharmaceutically acceptable salt thereof.

2. A compound according to claim 1, wherein X in the general formula I is a halogen atom.

3. A compound according to claim 2, wherein $R^1$ in the general formula I is a hydrogen atom or an ethyl group.

4. A compound according to claim 1, which is represented by the following formula:

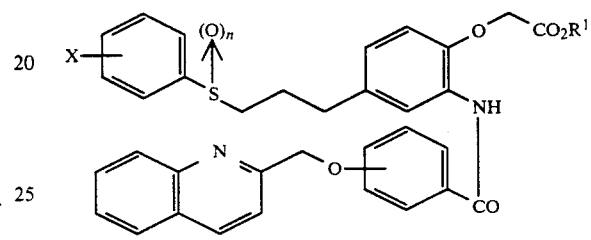

wherein X, $R^1$, and n have the same meanings as defined above.

5. A compound according to claim 1, which is represented by the following formula:

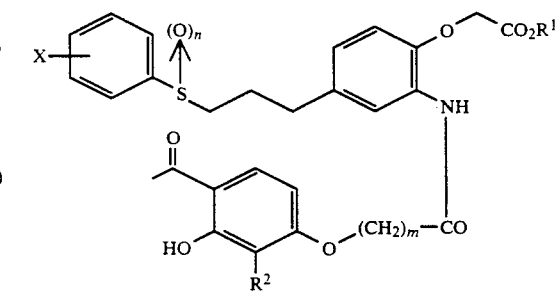

wherein X, $R^1$, $R^2$, n, and m have the same meanings as defined above.

6. A compound according to claim 4, which is 4-[3-(4-chlorobenzenesulfonyl)propyl]-2-[4-(2-quinoline methoxy)benzoylamino] ethyl phenoxyacetate.

7. A compound according to claim 4, which is 4-[3-(4-chlorobenzenesulfonyl)propyl]-2-[4-(2-quinoline methoxy)benzoylamino] phenoxyacetic acid.

8. A compound according to claim 4, which is 4-[3-(4-chlorobenzenesulfonyl)propyl]-2-[3-(2-quinoline methoxy)benzoylamino] phenoxyacetic acid.

9. A compound according to claim 4, which is a tromethamine salt of 4-[3-(4-chlorobenzenesulfonyl)-propyl]-2-[3-(2-quinolinemethoxy) benzoylamino]] phenoxyacetic acid.

10. A compound according to claim 5, which is 4-[3-(4-chlorobenzenesulfonyl)propyl]-2-[(4-acetyl-3-hydroxy-2-propyl)phenoxyacetylamino] ethyl phenoxyacetate.

11. A compound according to claim 5, which is 4-[3-(4-chlorobenzenesulfonyl)propyl]-2-[(4-acetyl-3-hydroxy-2-propyl)phenoxyacetylamino] phenoxyacetic acid.

12. A compound according to claim 5, which is 4-[3-(4-chlorobenzenesulfonyl)propyl]-2-[(4-acetyl-3-hydroxy-2-propyl)phenoxy-4-butaminde] phenoxyacetic acid.

13. A pharmaceutical composition for the antagonism of thromboxane $A_2$ or leukotriene, said composition comprising an effective amount of the compound according to claim 1 or a pharmaceutically acceptable salt thereof to antagonize thromboxane $A_2$ or leukotriene, and a pharmaceutically acceptable carrier therefor.

14. A method for the antagonism of thromboxane $A_2$, said method comprising administering an effective amount of the compound according to claim 1 to antagonize thromboxane $A_2$ to a patient in need of such treatment.

15. A method for the antagonism of leukotriene, said method comprising administering an effective amount of the compound according to claim 1 to antagonize leukotriene to a patient in need of such treatment.

16. A method for the treatment of allergy, said method comprising administering an effective amount of the compound according to claim 1 to treat an allergy, to a patient in need of such treatment.

* * * * *

UNITED STATES PATENT AND TRADEMARK OFFICE
CERTIFICATE OF CORRECTION

PATENT NO. : 5,179,105

DATED : January 12, 1993

INVENTOR(S) : Azuma IGARASHI ET AL

It is certified that error appears in the above-identified patent and that said Letters Patent is hereby corrected as shown below:

TITLE PAGE:

In Section [57], delete "t,0010" and insert --

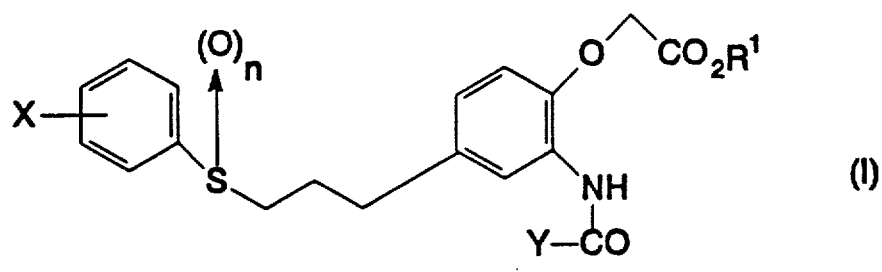

--.

UNITED STATES PATENT AND TRADEMARK OFFICE
CERTIFICATE OF CORRECTION

PATENT NO.   :  5,179,105
DATED        :  January 12, 1993
INVENTOR(S)  :  Azuma IGARASHI ET AL It is certified that error appears in the above-identified patent and that said Letters Patent is hereby corrected as shown below:

In Section [57], delete "hydroxy" and insert -- hydroxyl --.

In Column 8, line 39, delete "wased" and insert -- washed --.

In Column 10, line 54, after "was" and before "anhydrous", insert -- washed with saturated saline solution and dried with --.

In Column 14, line 51, delete "1.19" and insert -- 1.19 g --.

Signed and Sealed this

Fourth Day of January, 1994

Attest:

BRUCE LEHMAN

*Attesting Officer*     *Commissioner of Patents and Trademarks*